(12) United States Patent
Oshida

(10) Patent No.: US 6,183,255 B1
(45) Date of Patent: Feb. 6, 2001

(54) TITANIUM MATERIAL IMPLANTS

(76) Inventor: Yoshiki Oshida, 715 W. Walnut St., Apt. I, Lockefield Garden Apartments, Indianapolis, IN (US) 46202

(*) Notice: Under 35 U.S.C. 154(b), the term of this patent shall be extended for 0 days.

(21) Appl. No.: 09/536,296

(22) Filed: Mar. 27, 2000

(51) Int. Cl.⁷ .................................................. A61C 8/00
(52) U.S. Cl. ........................................ 433/201.1; 623/16
(58) Field of Search ............................... 433/201.1, 172, 433/173, 174, 175, 176; 623/16

(56) References Cited

U.S. PATENT DOCUMENTS 5,152,794 * 10/1992 Davidson ............................... 623/16
5,354,390 * 10/1994 Haszmann et al. .................. 148/518

* cited by examiner

Primary Examiner—Nicholas D. Lucchesi
(74) Attorney, Agent, or Firm—Breiner & Breiner

(57) ABSTRACT

One of many universal requirements of dental or orthopedic implants, wherever they are used in the vital body, is that the implant system should be biologically functioning. To achieve the biological functionality, the implant should meet several requirements for compatibility. These include biological compatibility and mechanical compatibility. It has now been recognized that morphological compatibility and crystallographic compatibility should be added to these two compatibility requirements. Hence, the present invention provides a method of forming a certain type of crystalline structure of titanium oxide and controlled surface roughness to meet both morphological and crystallographic compatibilities. It has been further determined that a chemical treatment (using sodium hydroxide) alone or followed by in-air oxidation, or acid treatment (a mixed aqueous solution of hydrofluoric acid and nitric acid), followed by sodium hydroxide treatment, furthermore followed by in-air oxidation provide for advantageous surface modifications to create a complex mixture of rutile with anatase and/or brookite types of titanium oxide and provide a most favorable surface for wettability and an acceptable range of surface roughness.

5 Claims, 2 Drawing Sheets

TITANIUM MATERIAL IMPLANTS

FIELD OF THE INVENTION

The present invention relates to medical orthopedic and dental implants which are made of titanium materials. More specifically, the present invention relates directly to surface modifications of titanium material implants by either mechanical, chemical, thermal, or any combination thereof in order to promote and improve the bony ingrowth for a better biological fixation in the receiving hard/soft vital tissues. Furthermore, due to the fact that different surface modifications, as described above, form different types of crystalline structure of titanium oxides as a treatment product, the present invention also is directed to crystalline compatibility for successful titanium material implants.

BACKGROUND OF THE INVENTION

One of many universal requirements of implants, wherever they are used in the body, is the ability to form a suitably stable mechanical unit with neighboring hard or soft tissues. A loose (or unstable) implant may function less efficiently or cease functioning completely, or it may induce an excessive tissue response. In either case, it may cause the patient discomfort and pain. In several situations, a loose implant is deemed to have failed and has to be surgically removed.

For a long time, it has been recognized that any type of implant (whether a dental implant or orthopedic implant), should possess a biological compatibility with implant-receiving-surrounding hard and soft vital tissues. Accordingly, the material choice for implants is limited to certain types of materials, including titanium materials such as un-alloyed commercially pure titanium (ASTM Grades 1, 2, 3, 4 and 7) and Ti-based alloy such as Ti-6Al-4V, AISI Type 316L stainless steel, or some ceramic materials such as pure alumina or synthetic compounds having Ca and P ions (including hydroxyapatite or tri-calcium phosphate).

Dental or orthopedic prostheses, particularly surface zones thereof, should respond to the loading transmitting function. The placed implant and receiving tissues form a unique stress-strain field. Between them, there should be an interfacial layer. During the loading, the strain-field continuity should be held, although the stress-field is obviously in a discrete manner due to different values of modulus of elasticity of both implant material and tissues. If the magnitude of the difference in modulus of elasticity between implant and tissue is large, then the interfacial stress, accordingly, will be so large that the placed implant system will face a risky failure situation. Therefore, materials for implants or surface zone of implants should be mechanically compatible to mechanical properties of the receiving tissues, so that the interfacial stress can be minimized. This is the second compatibility and is called mechanical compatibility.

Furthermore, a third compatibility, i.e., morphological compatibility is also important. In a scientific article published by the present inventor ("Fractal Dimension Analysis Of Mandibular Bones: Toward A Morphological Compatibility Of Implants" in *Bio-Medical Materials and Engineering*, 1994, 4:397–407), it was found that surface morphology of successful implants has upper and lower limitations in average roughness (1~50 $\mu$m) and average particle size (10~500 $\mu$m), regardless of the type of implant material (metallic, ceramics, or polymeric materials). If a particle size is smaller than 10 $\mu$m, the surface will be more toxic to fibroblastic cells and have an adverse influence on cells due to their physical presence independent of any chemical toxic effects. If the pore is larger than 500 $\mu$m, the surface does not exhibit sufficient structural integrity because it is too coarse. This third morphological compatibility (which was proposed by the present inventor) is now well accepted in the implantology society.

The attachment of cells onto titanium surfaces is an important consideration in the areas of clinical implant dentistry. A major consideration in designing implants has been to produce surfaces that promote desirable responses in the cells and tissues contacting the implants. Cellular behaviors such as adhesion, morphologic change, functional alteration, and proliferation are greatly affected by surface properties such as hydrophilicity, roughness, charge, free energy, and morphology.

It is well known that the surface chemistry, surface energy, and surface topography govern the biological response to an implant material. The tissue response to a dental implant may involve physical factors such as size, shape, surface topography, and relative interfacial movement, as well as chemical factors associated with the composition and structure.

Biomaterials used in a living organism may come into contact with cells in the related tissue for a long period of time. For this reason, they should naturally be harmless to the organism, and the mechanical properties should be suited to the purpose, as described previously. Furthermore, they should possess biological effect capable of providing favorable circumstances for the properties and functions of the cells at the implant site. For example, materials used in the construction of an artificial heart or heart valve must provide for anti-thrombogenesis, which prevents attachment of the cellular components of blood. By contrast, materials for a dental or bone implant must be suitable for cell attachment, because both the connective and epithelial cells (with which these materials mainly come into contact) are anchorage-dependent and therefore need a cell attachment scaffold for cell division and cell differentiation to be conducted. Therefore, "attachability" of the cells to the material is one of the important parameters in the evaluation of biomaterials.

Surface properties of biomaterials play a critical role in the adhesion process of adjacent cells. Little is known about the optimal surface characteristics of titanium that promote tissue-implant interaction. Cell adhesion to and spreading on a biomaterial are, amongst other factors, dependent on the surface wettability of the biomaterial. Measurement of the wettability of a material, expressed by the contact angle in the presence of the different liquids, might be a predictive index of cytocompatibility. Surface modification of titanium surfaces has been shown to improve bony apposition, tissue adhesion, and migration. With the surface chemistry of titanium altered, different rates of cellular attachment have been observed. However little is known about the biochemical responses of cells to other surface properties, such as oxide thickness, oxide crystal structure, surface topography, or the dynamic surface changes which can occur after implantation.

It has been shown that methods of implant surface preparation can significantly affect the resultant properties of the surface and subsequently the biological responses that occur at the surface. Recent efforts have shown that the success or failure of dental implants can be related not only to the chemical properties of the implant surface but also to the micromorphologic nature of the surface.

Many clinical studies on dental implants have focused on the success of endosseous implants with a variety of surface characteristics. In an attempt to improve the quantity and quality of the bone-implant interface, numerous implant surface modifications have been proposed.

In order to achieve morphological compatibility, titanium implant surfaces need to be modified. They can be treated by additive methods such as the titanium plasma spray procedure to increase surface area. They have also been modified by subtractive methods such as acid pickling, acid etching, sandblasting and other small particle-blasting to change the texture as well as to increase the effective surface area. The development and use of these surface modifications have been based on the theory that improved osseointegration can be achieved by increasing the topography or roughness of the implant surface.

As briefly mentioned above, to modify the surface layer, there are mainly two types of textures, i.e., (1) convex texture and (2) concave texture. Additive treatments such as plasma spray coating or depositing of hydroxyapatite particles or titanium beads are preformed to create convex surface morphology. There are some possibilities with the surface convex treatments to loosen or detach the deposited particles. In contrast, mechanical treatments such as sandblasting or chemical treatment can create concave surface texture.

Reviewing previous works, there are several relevant articles published. Micheals at el. ("In vitro Cell Attachment Of Osteoblast-like Cells To Titanium", *J. Dent. Res.*, 1989, 68:276) determined that a higher percentage of osteoblast-like cells attached to rough commercially pure titanium (CPT) surfaces produced by sandblasting than to smoother surfaces which were polished with 1 $\mu$m diamond paste. It was suggested that it is possible to control short-term in vitro cellular attachment and morphology by altering surface micromorphology.

Thomas et al. ("The Effects Of Surface Macrotexture And Hydroxyapatite Coating On The Mechanical Strengths And Histologic Profiles Of Titanium Implant Materials", *J. Biomed, Mater, Res.*, 1987, 21:1395–1414) found that roughened surfaces have an increased implant surface area that results in greater surface coverage by bone as compared to smooth-polished surfaces.

Buser et al. ("Influence Of Surface Characteristics On Bone Integration Of Titanium Implants. A Histomorphometric Study In Miniature Pigs", *J. Biomed. Mater. Res.*, 1991, 25:889–902) reported that increased surface area positively correlated with an increased bone-implant contact. It was also reported that the highest extent of bone-implant interface was observed in sandblasted and acid attacked surfaces ($HCl/H_2SO_4$) and hydroxyapatite-coated implants.

Several investigators have demonstrated that implant surface roughness enhances the osseointegration of implants to bone as determined by torque removal tests. Torque removal forces have been used as a biomechanical measure of anchorage or osseointegration in which the greater forces required to remove implants may be interpreted as an increase in the strength of osseointegration. Wilke et al. ("The Influence Of Various Titanium Surfaces On The Interface Shear Strength Between Implants And Bone", *Clinical Implant Materials Advances In Biomaterials Amsterdam: Elsevier*, 1990, 9:309–314) found, when comparing six groups of different surface structures, that the highest required removal torque was needed for the acid treated screws with a rough surface. Screw shaped implants with surfaces that were sandblasted and acid etched (HCl/$H_2SO_4$) achieved higher resistance to reverse torque rotation than screw shaped implants with surfaces that were either electropolished, sandblasted and acid pickled (HF/$HNO_3$) or titanium plasma-spray coated.

Klokkevold et al. ("Osseointegration Enhanced By Chemical Etching Of The Titanium Surface. A Torque Removal Study In The Rabbit", *Clin. Oral Implants Res.*, 1997, 8:442–227) compared torque resistance to removal of screw shaped titanium implants having an acid etched (HCl/$H_2SO_4$) surface with implants having a machined surface which is relatively smooth. Resistance to torque removal was found to be four times greater for the implants with the acid etched surface as compared to the implants with the machined surface. It was suggested that chemical etching of the titanium implant surface significantly increased the strength of osseointegration as determined by resistance to reverse torque rotation.

Cochran et al. ("Bone Response To Unloaded And Loaded Titanium Implants With A Sandblasted And Acid-etched Surface: A Histometric Study In The Canine Mandible", *J. Biomed. Mater. Res.*, 1998, 40:1–11) found that a sandblasted and acid-etched titanium implant had a greater bone-to-implant contact than did a comparably-shaped implant with a titanium plasma sprayed surface.

In an in vitro study, Bowers at al. ("Optimization Of Surface Micromorphology For Enhanced Osteoblast Responses in vive", *Int. J. Oral Maxxiofac, Implants*, 1992, 7:302–310) found significantly higher levels of attachment of osteoblast-like cells to a rough sandblasted surface with irregular morphology when compared to smooth and regular surfaces.

The above showings of beneficial effect of mechanical and chemical roughening titanium surfaces confirm the desirability of morphological compatibility, which the present inventor has proposed and is now well accepted.

Another approach was recently developed to improve bone-titanium bonding. Kokubo et al. ("Spontaneous Apatite Formation On Chemically Surface Treated Ti", *J. Amer. Ceram. Soc.*, 1996, 79:1127–1129) showed that, after a combination of alkali and heat treatment, bone-like apatite forms on the surface of titanium in a simulated body fluid, that has an ion concentration nearly equal to that of human blood plasma. Apatite formation on the material surface is believed to be a prerequisite for bioactivity, that is, direct bone bonding.

In an animal study, Yan et al. ("Bonding Of Chemically Treated Titanium Implants To Bone", *J. Biomed. Mater. Res.*, 1997, 37:267–275) reported that alkali-treated (in 4M NaOH at 60° C. for 24 hours) and heat-treated (in air oxidation at 600° C. for 1 hour) titanium can bond to bone directly. Also shown was that titanium (that is soaked in a simulated body fluid after alkali and heat treatments) has bone-bonding ability. It was found that a Ca-P rich layer was detectable at the interface between bone and alkali- and heat-treated titanium implants and enhanced the strength of bone-implant bonding by inducing a bioactive surface layer on titanium implants.

Kim et al., ("Preparation Of Bioactive Ti And Its Alloys Via Simple Chemical Surface Treatment", *J. Biomed. Mater. Res.*, 1996, 32:409–417) reported that after alkali (10M NaOH or 10M KOH at 60° C. for 1 to 24 hours) and heat treatments (in air oxidation at 400° C. to 800° C.), a bone-like apatite layer also formed on the surface of titanium alloys such as Ti-6Al-4V, Ti-6Al-2Nb-Ta, and Ti-15Mo-5Zr-3Al in a simulated body fluid. As with alkali- and heat-treated pure titanium, these alloys are thought to be able to bond directly via alkali and heat treatments.

During wet oxidation in either boiling acid or anodization, a concave surface is normally produced due to the selective dissolution and subsequent oxidation. This is chemical modification. The concave texture can also be created mechanically. It is generally believed that the roughness of as-blasted or as-peened surface is about ⅕ to ¹⁄₁₀ of the size of used media (Y.Oshida et al., "Effects Of Shot-penning On Surface Contact Angles Of Biomaterials", *J. Mater. Sci.: Mater. in Medicine*,. 1993, 4:443–447). This is a mechanical modification. If the multi-mold concave texture is desired, the mechanical texturing and chemical treatments can be combined. This is then mechano-chemical modification, or chemi-mechanical modification. Furthermore, during the above treatment, surface of titanium materials will be covered with oxide film with appropriate thickness. The crystalline structure of these oxide films will be varied, depending on the chemistry used. Moreover, the crystalline structure of titanium oxide film can also be controlled and altered by thermal treatments such as oxidation. This is thermal modification. Hence, some treatments could involve mechano-chemical thermal modification.

Certain information is already known about the crystalline structure of titanium oxides. Titanium is a very active element. When fresh titanium is exposed to the atmosphere by such cutting acts as lathing, milling, or sawing, an oxide layer begins to form within nanoseconds. After only one second, a surface oxide with some 20 to 50 $\mu$m in thickness will form. The characteristic composition and structure of the oxide layer often differ depending on the technique used to prepare the surface of the metal. The exact composition of the oxide, $TiO_x$, (where x is a number in the range from 1.0 to 2.0), its morphology and content of low concentrations of impurity elements, are examples of properties that may be varied in a controlled manner.

There are seven possible types of oxide, $TiO_x$, formed on titanium materials. They include (1) amorphous oxide, (2) cubic TiO ($a_o$=4.24 Å), (3) hexagonal $Ti_2O_3$ ($a_o$=5.37 Å, $\alpha$=56°48'), (4) tetragonal $TiO_2$ (anatase) ($a_o$=3.78 Å, $c_o$=9.50 Å), (5) tetragonal $TiO_2$ (rutile) ($a_o$=4.58 Å, $c_o$=2.98 Å), (6) orthorhomic $TiO_2$ (brookite) ($a_o$=9.17 Å, $b_o$=5.43 Å, $c_o$=5.13 Å), and (7) non-stoichiometric oxide.

It was found that amorphous titanium oxide film which was formed during chromic acid anodization, was converted to a crystalline rutile by heating the amorphous film in distilled water at 85° C. for 100 hours. The transformation of amorphous titanium dioxide to anatase to further rutile was consistent and the rate of the transformation is accelerated by increasing temperature and decreasing solution pH. (A. Matthews "The Crystallization Of Anatase And Rutile From Amorphous Titanium Dioxide Under Hydro Thermal Conditions", *Amer. Miner*, 1976, 61:419–424).

Crystallinity, which is judged by the sharpness of diffraction lines, decreased according to the treatment in the following order (K. W. Allen et al., "Titanium And Alloy Surfaces For Adhesive Bonding", *A Adhesion*, 1974, 6:229–237): (higher degree) alkaline hydrogen peroxide→phosphate fluoride→hydrofluoric acid→anodic oxidation→hydrochloric acid→sulphuric acid (lower degree).

Much work has been done to identify the crystallography of titanium oxides formed with various acids . A mixture of anatase and rutile was identified under a wet oxidation using boiling 0.1 weight % $H_2SO_4$ for 24 hours, while a mixture of anatase and brookite was obtained in the boiling 0.2 weight % HCl oxidation for 24 hours (T. Koizumi et al., "Structure Of Oxide Films Formed On Ti In Boiling Dilute $H_2SO_4$ and HC1", *Corrosion Sci.*, 1968, 8:195–196). Only anatase phase was identified under anodization using 0.1 M $H_2SO_4$ at 30° C. at 12.5 mA/cm² (J.Yhalom et al., "Electrolytic Breakdown Crystallization Of Anodic Oxide Films on Al, Ta and Ti", *Electrochimica Acta*, 1970, 15:1429–1435), or 0.1 M $H_2SO_4$ at 5 V (T. Ohtsuka, "Structure Of Anodic Oxide Films On Titanium" *Surface Sci.*, 1998, 12:799–804). On the other hand, solely rutile structure was obtained by wet oxidation using boiling 10 weight % HCl (A.Felske et al., "Raman Spectroscopy Of Titanium Dioxide Layers", *Electrochimica Acta*, 1989, 34:75–77), boiling 10 weight % $H_2SO_4$ (E. P. Lautenschlager et al., "Titanium And Titanium Alloys Such As Dental Materials", *Int. Dent. J.*, 1993, 43:245–253), or anodization using 0.5 M $H_2SO_4$ at 5 to 10 V (K. W. Allen et al., ibid). It was found that neutral, alkaline, and mildly acidic conditions favor anatase formation, whereas more strongly acid environments favor rutile formation (A. Matthews, ibid).

As mentioned above, measurements of the wettability of a material surface, expressed by the contact angle in the presence of different liquids, might be a predictive index of cytocompatibility and cell attachability.

Surface wettability is largely dependent on surface energy and influences the degree of contact with the physiological environment, as described above. Increased wettability (or decreased contact angle) enhances interaction between the implant surface and the biological environment.

Wettability on the surfaces of biomaterials is reported to affect cell attachment considerably. The reason is believed to be that microvilla and filopodia, which work advantageously at the early stage of the cell attachment, are needed for the cells to pass through the energy barrier between the material and the cells themselves. Hence, cell attachment in its early stage is affected by physical and chemical properties, including the wettability. It has been pointed out that cell attachment to the material is closely related to wettability of its surface. It is, for this reason, that the focus of biomaterials development has shifted to the control of wettability of the material surface and attachment of tissue to the implant site. Previous research reports on the wettability of materials and their effects on tissue, but failed to define the wettability clearly and did not clarify the effect caused by surface configuration and crystalline structure of surface oxides.

According to Yanagisawa et al., ("Effects Of "Wettability" Of Biomaterials On Culture Cells", *J. Oral Implantol.*, 1989, 15:168–177), it was found that the contact angles ($\theta$) of materials affected both the cell attachment and spreading rates ($d\theta/dt$). With small contact angles and high wettability, the cell attachment rate was high, while it was low when the contact angles were large and wettability was low. Thus, they concluded that wettability of biomaterials is considered to be an important parameter of biological effect at the cell level.

The media used for the contact angle measurement must meet several requirements: (1) not be highly viscous, (2) not be of high specific weight, and (3) not be chemically active against the substrate surface. It appears to be that distilled (or deionized) water is normally employed. Glycerol and 1% NaCl solution have also been used. The different types of liquids (water, diiodomethane, glycerol, ethylene glycol) showed different degrees of contact angles. However, it was reported that these differences were not consistent among the different surface preparations (Yanagisawa et al., ibid.).

Few investigations have related the influence of surface roughness and crystalline structure on wettability and spreadability (for example, Y.Oshida et al., "Effects Of Shot-peening On Surface Contact Angles Of Biomaterials",

*J. Mater. Sci.: Mater, in Medicine*, 1993, 5:443–447). Shot peening is an advanced technique to create controlled surface topographic features along with other engineering benefits, including generating surface compressive residual stress. It was suggested that the wettability and spreadability appear to be related to the crystalline structure of the oxide films formed on these biomaterials. It was, therefore, suggested that the surface energy (monitored from the contact angle measurement) relates to the crystalline structure of surface oxide films. It was also observed, for shop peening and pre-oxidized surfaces, that changes in contact angles as a function of time are strongly dependent upon the type of surface oxide. A higher spreading rate is observed on biomaterials whose surfaces are covered with $TiO_2$ while a lower spreading coefficient is seen on cubic structure oxides including spinel type oxide formed on stainless steel.

OBJECTS OF THE INVENTION

As a consequence, a primary object of the present invention is creating surface concave textures of titanium biomaterials engineered by either mechanical, chemical, thermal means, or any combination thereof. Accordingly, it is a further primary object of the present invention to provide an advantageous method of forming a certain type of crystalline structure of oxide(s) formed on titanium biomaterials in order to fulfill the crystalline compatibility requirement. It is another object of this invention to provide an advantageous method of creating surface roughness as desired to meet the morphological compatibility requirement by modifying the surface of titanium biomaterials by means of either mechanical, chemical, thermal, or any combination thereof.

The term "titanium biomaterials" is understood to be any titanium material, including un-alloyed pure titanium, titanium-based alloys and titanium-based amorphous alloys, which are biologically acceptable.

Figure 1:
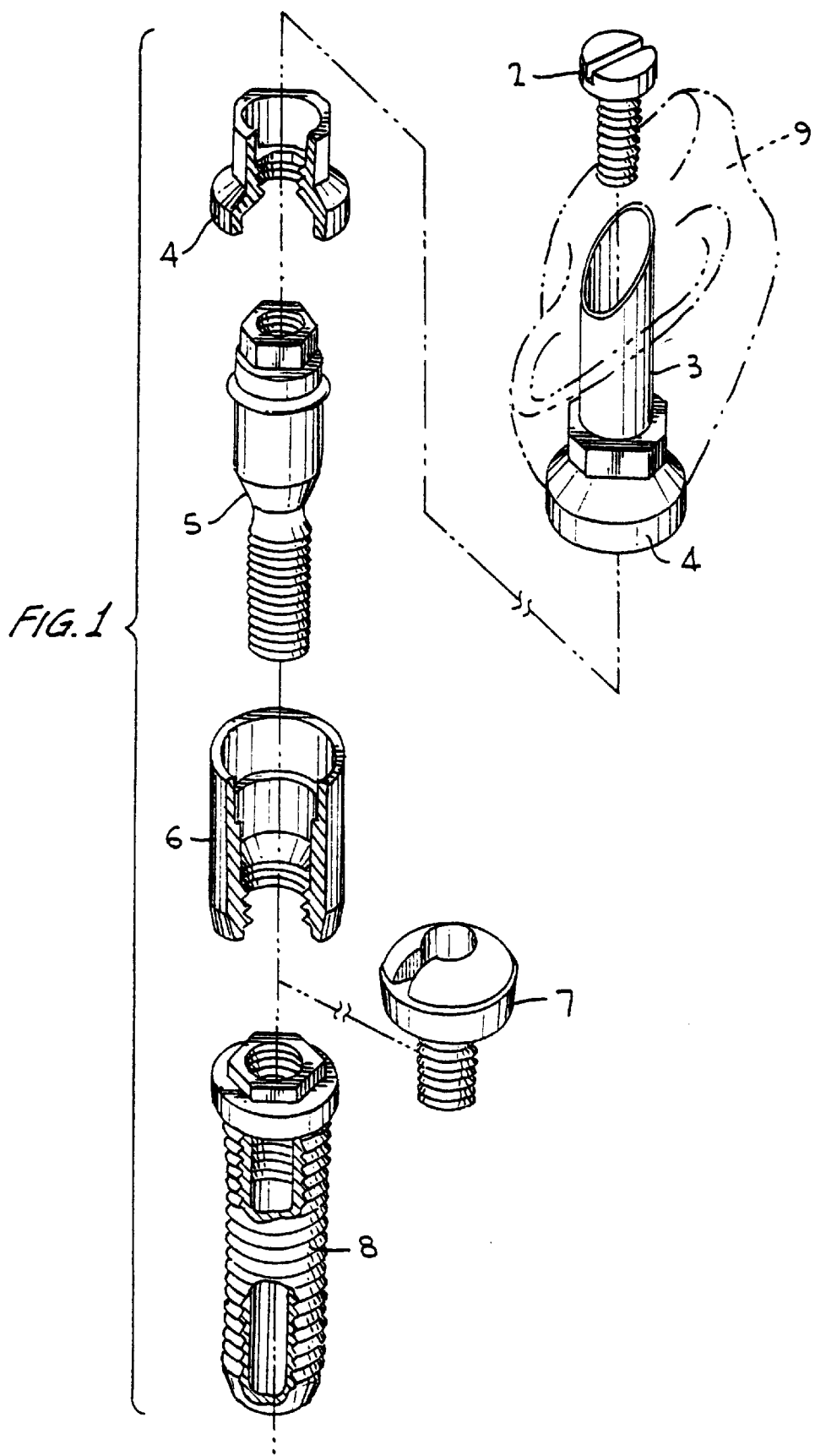
FIG. 1 shows a typical osseo- (or osteo-) integration type free-standing single unit dental implant (Branemark System), in which there is a perspective view of each necessary component of dental implant 1 prior to assembly, i.e., a gold screw 2, a gold cylinder 3, an abutment screw 4, an abutment 5, a cover screw 6, a fixture 7, and an implant main body 8. Fixture 7 is the only component which is used temporarily until the main body 8 is mechanically fixed in the vital bone. When the main implant body 8 is stabilized, fixture 7 is removed and the rest of components 6, 5, 4, 3, and 2 are assembled along with a denture tooth (or artificial tooth) 9.
Figure 2:
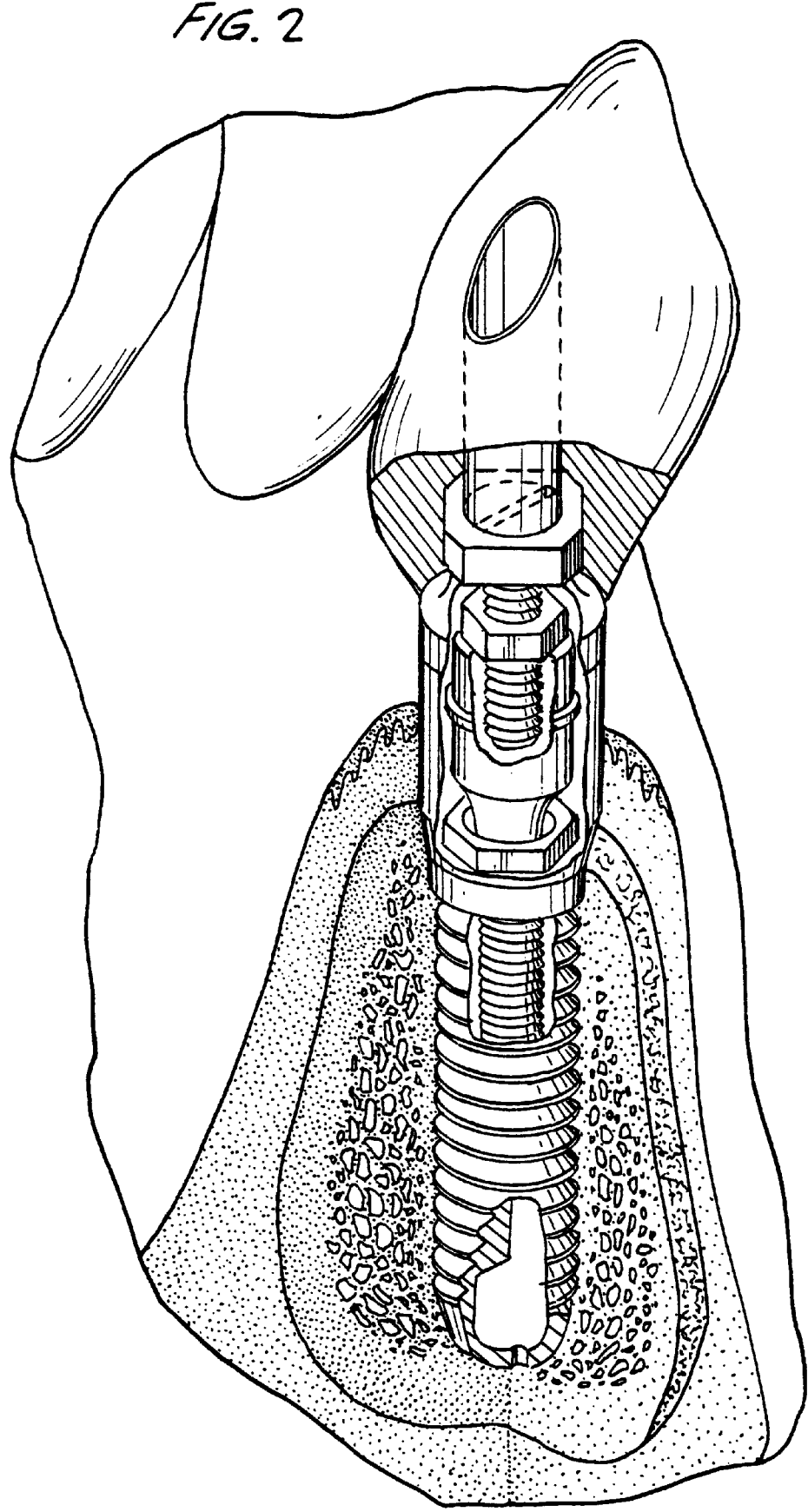
FIG. 2 shows the assembled implant system of FIG. 1 in place in use.

Although the attached Figures show that the main implant body 8 is a screw-type and has a hole at its bottom portion, this is just one of many variations of implant designs, and the present invention is not to be limited to a particular type of implant.

The present invention relates directly to surface modification of main implant body 8 for any possible design and titanium biomaterials.

DESCRIPTION OF THE INVENTION INCLUDING PRESENTLY PREFERRED EMBODIMENTS

The present invention relates to surface modification of titanium material implants. Both the micro-architecture (microgeometry, roughness, etc.) of the surface and its chemical composition are important for the following reasons: (1) an atomically smooth surface and a curved or rough surface, respectively, cause different contact areas with biomolecules, cells, etc., if the radius of curvature of surface irregularities and structural elements matches the dimensions of the biological units; the different contact areas, in turn, producing different perturbations and types of bonding of the biological units, which may influence their conformation and function; and (2) variations in chemical composition of the surface produce different types of bonding to the biomolecules, which may then also affect their properties. The surface chemical composition also largely determines the chemical stability/reactivity of the implant material.

Surface plays a crucial role in biological interactions for four reasons. First, the surface of a biomaterial is the only part in contact with the bioenvironment. Second, the surface region of a biomaterial is almost always different in morphology and composition from the bulk, these differences arising from molecular rearrangement, surface reaction, and contamination. Third, for biomaterials that do not release or leak biologically active or toxic substances, the characteristics of the surface govern the biological response. Fourth, some surface properties such as topography affect the mechanical stability of the implant-tissue interface.

From an in vitro standpoint, the response of cells and tissues at implant interfaces can be affected by surface topography or geometry on a macroscopic basis, as well as by surface morphology or roughness on a microscopic basis, and crystalline structure at an atomic level. The crystalline structure is a result of various surface treatments by either mechanical, chemical, thermal, or any combination of these means.

This invention relates directly to the latter case of surface modification by a concave texturing method by either mechanical, chemical, or thermal, or any combination thereof. More importantly, because of using different chemicals and other treatment methods, the crystalline structure of surface oxide films formed on titanium materials can be varied. As described in greater detail below, it has been determined that this difference in crystalline structure of surface oxide films can be used to control the most important in vitro indication for success of the osteointegration type titanium material implants.

More particularly, the present invention relates to a crystalline compatibility, which is a new and fourth compatibility to be added to the existing three compatibility requirements described above. Crystalline compatibility is significant because various surface modifications create and form different types of crystalline structures of titanium oxides. Accordingly, by satisfying the four compatibilities (biological, mechanical, morphological, and crystalline), any implant system can be expected to exhibit excellent biofuntionality.

The present invention will now be described through examples of the invention and comparative examples.

Sample coupons (10×50×1 mm) were prepared from un-alloyed commercially pure titanium (CPT; ASTM Grade 1), Ti-6Al-4V alloy, and TiNi alloy. Each sample was mechanically polished with grit #800 metallographic SiC paper. This serves as a control sample for the rest of the treated samples.

There were all together five treatment groups. They include (1) a control group, (2) a mechanical treatment group, (3) a chemical treatment group, (4) a mechano-chemical treatment group, and (5) a chemi-thermal treatment group. Detailed descriptions of each treatment are set forth below in the description of preferred embodiments.

For each treated sample, three different evaluations were preformed as described below.

1) Surface roughness measurements: using a profilometer, 10 readings were collected for average surface roughness ($R_a$) as well as the maximum roughness ($R_{max}$).

2) Surface contact angle measurements: using four different media (distilled water, 1% NaCl solution, neutrophil suspension, and osteoblast-like cells). Distilled water and 1% NaCl solution were used since these are commonly employed for the contact angle measurements. The neutrophil was included because it is central to early acute and chronic inflammation phase defense and may be critical to implant acceptance in a host. The osteoblast-like cells were also included because they are strongly related to the osteointegration in implant healing phases. All together six readings were collected and the average value was obtained for each treated sample for each aforementioned media.

3) Transmission Electron Diffraction (TED) method: TED was employed for identification of crystalline structure of oxide film(s) formed on each treated sample. The thin oxide film was stripped from the substrate titanium material using a grid-etching method (Y.Oshida et al., "Changes In Contact Angles As A Function Of Time On Some Pre-oxidized Biomaterials", *J. Mater. Sci.: Mater. in Medicine*, 1992, 3:306–312). For identification of crystalline structure, a pure gold foil was used as a standard reference (Y.Oshida, ibid.). The TED was performed under an accelerated electron voltage of 100 kV.

PREFERRED EMBODIMENTS

EXAMPLE 1

Using commercially pure titanium (which is hereinafter referred to as CPT) coupons, three different treatments were performed. They included (a) chemical treatment (by 5 mol NaOH at 70° C. for 24 hours), (b) chemi-thermal treatment (5 mol NaOH at 70° C. for 24 hours, followed by in air oxidation at 600° C. for 1 hour), and (c) double chemi-thermal treatment (mixed acid HF/HNO$_3$/H$_2$O by 1:1:2 volume, followed by 5 mol NaOH at 70° C. for 24 hours, furthermore followed by in air oxidation at 600° C. for 1 hour). The TED results indicated that all differently treated surfaces of CPT were covered with dominantly rutile mixed with anatase and/or brookite crystalline structures. Results on contact angle measurements showed that 27°±5° for (a) treatment, 15°±3° for (b) treatment, and 10°±4° for (c) treatment, respectively. These contact angles were averaged over 24 data points (four different media—distilled water, 1% NaCl solution, neutrophil suspension, and osteoblast-like cells; and 6 readings for each media). Hence, standard deviation is also reflected to the deviation caused by the media type. These results are excellent indications for bone healing mechanism and osteointegration. Although the measured contact angles were not significantly different among these three groups, the differences in surface average roughness were remarkable. Namely, it was found that the average roughness, $R_a$, for (a) treatment was 1.13±0.89 μm; while it was 1.52±1.21 μm for (b) treatment, and 2.38±0.12 μm for (c) treatment, respectively.

COMPARISON 1

Commercially pure titanium samples were mechanically polished with grit #800 (which is equivalently rough to the normally machine-finished CPT implant surfaces) SiC metallographic paper, serving as a control sample. The obtained contact angle (averaged over 6 readings for each four different media) was 62.50°±8°. The obtained surface roughness, $R_a$, was 0.57±0.25 μm. In the same category of mechanical treatment as this control sample group, CPT samples were sandblasted and shot-peened, as described previously. The contact angles averaged over 6 readings for each four different media was 40°±5° and 50°±4°, respectively, indicating that these surfaces do not provide favorable surface for wetting activity. The film thickness of oxides formed on these sample groups were so thin that the oxide film was not successfully isolated from the substrate. As a result, the oxide crystalline structure was not identified.

COMPARISON 2

Using CPT samples, surfaces were chemically treated in various acids. They included (a) 10 weight % HCl at boiling temperature for 6 hours, (b) mixed acid of HF, HNO$_3$, and H$_2$O (1:1:2 by volume) for 10 seconds, (c) 3% H$_2$O$_2$ at boiling temperature for 6 hours, and (d) 5% H$_2$SO$_4$ at boiling temperature for 15 hours. It was found that all surfaces treated in different chemicals were identified as pure rutile type titanium oxide crystals. The averaged contact angles over 10 readings for each four different media was 73°±7° for (a) treatment, 61°±10° for (b) treatment, 57°±6° for (c) treatment, and 73°±12° for (d) treatment, respectively. The average surface roughness was 1.70±0.72 μm for (a) treatment, 1.06±0.20 μm for (b) treatment, 0.61±0.28 μm for (c) treatment, and 2.15±0.75 μm for (d) treatment, respectively. These results were evaluated as not being excellent surfaces for successful osteointegration.

COMPARISON 3

CPT samples were simply in-air oxidized at 600° C. for 1 hour, serving as a control sample group for samples used in previous EXAMPLE 1. It was found that peeled off oxide film was identified to be pure rutile crystal structure. The average contact angle was 60°7°, and the average surface roughness was 0.55±0.28 μm. These surface conditions were not good for osteointegration.

EXAMPLE 2

Using Ti-6Al-4V alloy samples, all samples were treated in the same way as (a), (b), and (c) as described in EXAMPLE 1 for CPT samples. It was found that (1) all samples were covered with dominantly rutile type titanium oxide mixed with anatase and/or brookite type crystalline structures, (2) the average contact angle was 22°±6°, and (3) the average surface roughness was 0.35±0.07 μm. These surfaces provide excellent surface condition for successful osteointegration as results of EXAMPLE 1 indicate.

COMPARISON 4

Using Ti-6Al-4V samples, surfaces of these samples were treated in four different solutions (same as used for COMPARISON 2). The average value of contact angles over 6 readings for each four different media was over 65°, indicating clearly that these surfaces do not provide excellent surface condition for osteointegration. Particularly, after the treatment (d) (see COMPARISON 2), the measured surface contact angle was 75°±7°. Further, surfaces of all treated samples were covered with only rutile type crystalline structures.

EXAMPLE 3

Using TiNi alloy samples, all samples were treated under the same conditions used for EXAMPLE 1 or 2. It was found that (1) all surfaces were covered with dominantly rutile crystalline structure mixed with anatase and/or brookite structures, (2) the average value of surface contact angle was less 17°±4°, and (3) surface roughness was averaged at 0.3 μm. These surfaces are excellent for osteointegration mechanisms.

COMPARISON 5

Using TiNi samples, surfaces were treated under the same conditions as for COMPARISON 4. It was found that the average contact angle was higher than 60°, indicating that these surfaces are not good for implantable conditions.

Various medical and dental applications with respect to the invention include titanium material implants as applied not only to dental implants, but also to any orthopedic replacements including a total hip, knee, elbow, shoulder, ankle, or finger(s).

While this invention has been described in detail with respect to preferred examples, it should be understood that the invention is not limited to those precise embodiments. Rather, many modifications and variations would present themselves to one skilled in the art without departing from the scope and spirit of the invention. Moreover, while the detailed description of preferred examples has been mentioned as to three typical titanium materials (un-alloyed commercially pure titanium, Ti-6Al-4V, and TiNi), the titanium biomaterials should not be limited to these three materials, but also should include any titanium materials (in both amorphous and crystalline) if such are biologically not toxic to hard/soft vital tissues.

What is claimed is:

1. A dental or orthopedic implant comprising titanium material having on an exterior surface thereof rutile crystalline structure of titanium oxide mixed with anatase and/or brookite crystalline structures.

2. The dental or orthopedic implant of claim 1, wherein the titanium material is un-alloyed pure titanium, titanium-based crystalline alloys, or titanium-based amorphous alloys.

3. The dental or orthopedic implant of claim 1, wherein the rutile titanium oxide and anatase and/or brookite titanium oxide are formed by chemical treatment using sodium hydroxide.

4. The dental or orthopedic implant of claim 1, wherein the rutile titanium oxide and anatase and/or brookite titanium oxide are formed by chemical treatment using sodium hydroxide and thermal treatment under in-air oxidation.

5. The dental or orthopedic implant of claim 1, wherein the rutile titanium oxide and anatase and/or brookite titanium oxide are formed by sequential chemical treatment including a mixed aqueous solution of hydrofluoric acid and nitric acid, chemical treatment using sodium hydroxide, and thermal treatment under in-air oxidation.

* * * * *